United States Patent [19]
Andoh et al.

[11] Patent Number: 5,433,113
[45] Date of Patent: Jul. 18, 1995

[54] PROBE AND APPARATUS FOR DETECTING DEFECTS OF CYLINDRICAL MEMBER WITH SURFACE ULTRASONIC WAVE

[75] Inventors: Yoshimitsu Andoh; Yoshikazu Sano, both of Kitakyusyu, Japan; Hiroaki Sorano, Turtle Creek, Pa.

[73] Assignee: Hitachi Metals Ltd., Tokyo, Japan

[21] Appl. No.: 59,986

[22] Filed: May 12, 1993

[51] Int. Cl.$^6$ .............................................. G01N 29/28
[52] U.S. Cl. ........................................ 73/622; 73/624; 73/629
[58] Field of Search ................... 73/622, 624, 629, 644

[56] References Cited

U.S. PATENT DOCUMENTS

| | | | |
|---|---|---|---|
| 3,228,232 | 1/1966 | Proctor | 73/622 |
| 3,255,626 | 6/1966 | Van der Veer | |
| 4,472,975 | 9/1984 | Beck et al. | 73/622 |
| 4,559,825 | 12/1985 | Martens | 73/622 |
| 4,562,737 | 1/1986 | Davies | 73/622 |
| 4,879,088 | 11/1989 | von Swam et al. | 73/622 |
| 5,123,281 | 6/1992 | Cox et al. | 73/644 |
| 5,228,343 | 7/1993 | Schoenen et al. | 73/644 |

FOREIGN PATENT DOCUMENTS

| | | |
|---|---|---|
| 0472252 | 8/1991 | European Pat. Off. |
| 4113519 | 10/1992 | Germany |
| 62-80553 | 4/1987 | Japan |
| 62-81562 | 4/1987 | Japan |
| 62-73261 | 5/1987 | Japan |
| 4-276547 | 10/1992 | Japan |
| 1413242 | 11/1975 | United Kingdom ............ 73/644 |
| 8102636 | 9/1981 | WIPO |
| WO81/02636 | 9/1993 | WIPO |

OTHER PUBLICATIONS

Sorano H., et al., Hitachi Kinzoku Giho, vol. 8, pp. 52, 55, 56 (1992) "Quality Control for Newly Developed Composite Type Rolls".

Thesis No. 335, CAMP-ISIJ vol. 5 (1992), The 123rd Spring Conference of the Iron and Steel Institute of Japan, p. 515, Lines 19–26, published Mar. 3, 1992 "Surface Crack Detector for Rolling . . . ".

"Specification of Automatic System for Detecting Defects of Rolls" published by Krautkramer Japan Co., Ltd., Feb. 10, 1993 (p. 3, line 9 to p. 4, line 26).

*Primary Examiner*—Hezron E. Williams
*Assistant Examiner*—Helen C. Kwok
*Attorney, Agent, or Firm*—Sughrue, Mion, Zinn, Macpeak & Seas

[57] ABSTRACT

A method for detecting defects with a surface ultrasonic wave in which a surface ultrasonic wave probe is brought into contact with a surface of a rotating cylindrical member via a thin film of a contact liquid medium such that a contact trace of the probe extends linearly or helically about the circumference of the cylindrical member. An ultrasonic wave propagates in the surface portion of the cylindrical member from the probe in an opposite direction to the rotational direction of the cylindrical member. The probe is provided in a front portion thereof with a projection slightly extending downward from a lower surface of the probe so that the thin film of the contact liquid medium is stably formed. There is substantially no thin film of the contact liquid medium on the surface portion of the cylindrical member in which the surface ultrasonic wave propagates.

4 Claims, 1 Drawing Sheet

PROBE AND APPARATUS FOR DETECTING DEFECTS OF CYLINDRICAL MEMBER WITH SURFACE ULTRASONIC WAVE

BACKGROUND OF THE INVENTION

This invention relates to surface ultrasonic wave probe and apparatus for use in an ultrasonic inspection method for automatically detecting defects such as cracks, voids, scratches, etc. in a surface portion of a cylindrical member such as a roll for hot- or cold-rolling, a roller for conveying various articles, etc.

The detection of defects in the surface portion of a metal member is mainly conducted by the following methods:

(1) Manual Defect-Detecting Method with Surface Ultrasonic Wave

While an ultrasonic probe is manually scanned on a member to be tested in contact with the member, an ultrasonic beam is generated from the probe to cause a surface ultrasonic wave to propagate through a surface portion of the member to detect defects therein. However, since the probe is moved manually, the test takes many steps and an operator of the probe should have high skill. In addition, measurement errors easily take place because manual operation is not always the same.

(2) Tire Probe Method (Japanese Patent Laid-Open No. 62-80553)

An ultrasonic wave is generated from a tire-type probe to automatically detect defects in a surface portion of a cylindrical member to be tested. In this method, a thin film of a contact liquid medium should be formed in advance on a surface of the cylindrical member with which the tire-type probe is brought into contact. Also, since there is a large attenuation in a ultrasonic wave, high detection sensitivity cannot be obtained for fine defects.

(3) Eddy Current Inspection Method

Defects are detected by the change of eddy current. This method is widely utilized because it can easily be automated. However, the changes of metal texture, hardness, magnetic properties, etc. are also detected together with the defects, and closed cracks are not detected. Accordingly, the reliability of this method is lower than that of the manual defect-detecting method with a surface ultrasonic wave (1). Particularly, in the case of a roll, etc., only a low detection sensitivity is obtained for fine defects.

(4) Double Etching Method

A member is etched with nitric acid and hydrochloric acid to observe by the naked eye the difference in color between different metal textures of the member. However, this method has problems that acids are used, that the interior of the member cannot be inspected, that cast iron cannot be inspected, and that automatic inspection cannot be conducted.

(5) Penetration Inspection Method

Defects opening on a surface of a member to be tested are detected by using a penetrating liquid and a developing liquid which can penetrate into the defects by a capillary action. However, this method cannot be conducted efficiently, and shows only a low reliability for fine defects.

As described above, among the conventional defect-detecting methods, those suitable for automatic detection show only low detection precision, while those having high detection precision are not adapted to be automatically conducted. Particularly, the manual method for detecting defects with a surface ultrasonic wave is a effective method showing a high detection precision, but it can be conducted only by a skilled operator because a flat bottom surface of the probe is brought into contact with the cylindrical member, and because a surface ultrasonic wave is caused to propagate through the cylindrical member in a circumferential direction. If automatic operation is tried simply by bringing the probe into contact with the cylindrical member, the irregular reflection of a surface ultrasonic wave may take place due to a thin film of a contact liquid medium existing in a forward portion than the incident point of the ultrasonic wave at which a center beam of the ultrasonic wave enters into the contact liquid medium, failing to achieve a high detection precision.

In order to solve the above problems, the inventors previously proposed a method of detecting defects in a surface portion of a cylindrical member, wherein a surface ultrasonic wave probe is brought into contact with a surface of a rotating cylindrical member via a thin film of a contact liquid medium such that a contact trace of the probe extends linearly about the circumference of the cylindrical member, and an ultrasonic wave propagates in the surface portion of the cylindrical member from the probe in an opposite direction to the rotational direction of the cylindrical member, the cylindrical member being substantially free from a thin film of the contact liquid medium in a portion in which the surface ultrasonic wave propagates (Japanese Patent Laid-Open No. 4-276547). This method is suitable for automatic operation with much higher detection precision than those of the conventional methods. However, as a result of further research, it has been found that the thin film of the contact liquid medium cannot stably be formed between a lower surface of the probe and a surface of the cylindrical member, and that the contact liquid medium is highly likely to bulge or expand toward the forward direction (propagation direction of an ultrasonic wave). If there is a contact liquid medium in front of the probe, the irregular reflection and attenuation of the ultrasonic wave take place due to the thin film of the contact liquid medium having changeable thickness and expansion. As a result, this method suffers from a low detection precision.

OBJECT AND SUMMARY OF THE INVENTION

Accordingly, an object of the present invention is to provide a surface ultrasonic wave probe usable for the high-precision automatic detection of defects such as cracks, scratches, etc. in a surface portion of a cylindrical metal member such as a roll, a roller, etc.

Another object of the present invention is to provide a surface ultrasonic wave defect-detecting apparatus comprising such a probe.

As a result of intense research in view of the above object, the inventors have found that in a case where the incident point of a center beam of an ultrasonic wave generated from the probe is set at a point near a forward end (on the side of ultrasonic wave propagation) of the probe, where the probe is brought into contact with the cylindrical member via a thin film of a contact liquid medium, and where the ultrasonic wave is caused to propagate through the surface portion of the cylindrical member in an opposite direction to the rotational direction of the cylindrical member, the thin film of the contact liquid medium can be stabilized and the bulging or expansion of the contact liquid medium toward the forward direction from the probe can be effectively prevented by mounting a projection means such as a small plate to a front portion of the probe such that the projection means slightly projects downward into the thin film of the contact liquid medium from the lower surface of the probe, thereby obtaining information concerning the defects in the surface portion of the cylindrical member with high precision. The present invention has been completed based on this finding.

Thus, the surface ultrasonic wave probe of the present invention is usable for the detection of defects in a surface portion of a cylindrical member by a method in which the probe is brought into contact with a surface of a rotating cylindrical member via a thin film of a contact liquid medium such that a contact trace of the probe extends linearly about the circumference of the cylindrical member, and an ultrasonic wave propagates in the surface portion of the cylindrical member from the probe in an opposite direction to the rotational direction of the cylindrical member, the probe being provided in a front portion thereof with a projection means extending downward from a lower surface of the probe so that the thin film of the contact liquid medium is stably formed, and that there is substantially no thin film of the contact liquid medium on a surface of a portion of the cylindrical member in which the surface ultrasonic wave propagates.

The surface ultrasonic wave apparatus of the present invention comprises (a) a member for rotatably supporting a cylindrical member to be tested; (b) a carriage capable of reciprocating along the axis of the cylindrical member; (c) a surface ultrasonic wave probe supported by the carriage such that it is brought into contact with a rotating cylindrical member via a contact liquid medium, the probe generating an ultrasonic wave propagating in the surface portion of the cylindrical member as a surface ultrasonic wave in an opposite direction to the rotational direction of the cylindrical member; and (d) a pipe mounted to the probe and having an opening located on a lower surface of the probe near a front end thereof for supplying the contact liquid medium into a gap between the probe and the cylindrical member, the probe being provided in a front portion thereof with a projection means extending downward from a lower surface of the probe so that the thin film of the contact liquid medium is stably formed, and that there is substantially no thin film of the contact liquid medium on a surface of a portion of the cylindrical member in which the surface ultrasonic wave propagates.

DETAILED DESCRIPTION OF THE INVENTION

The preferred embodiments of the present invention will be described in detail below referring to the attached drawings.

Figure 1:
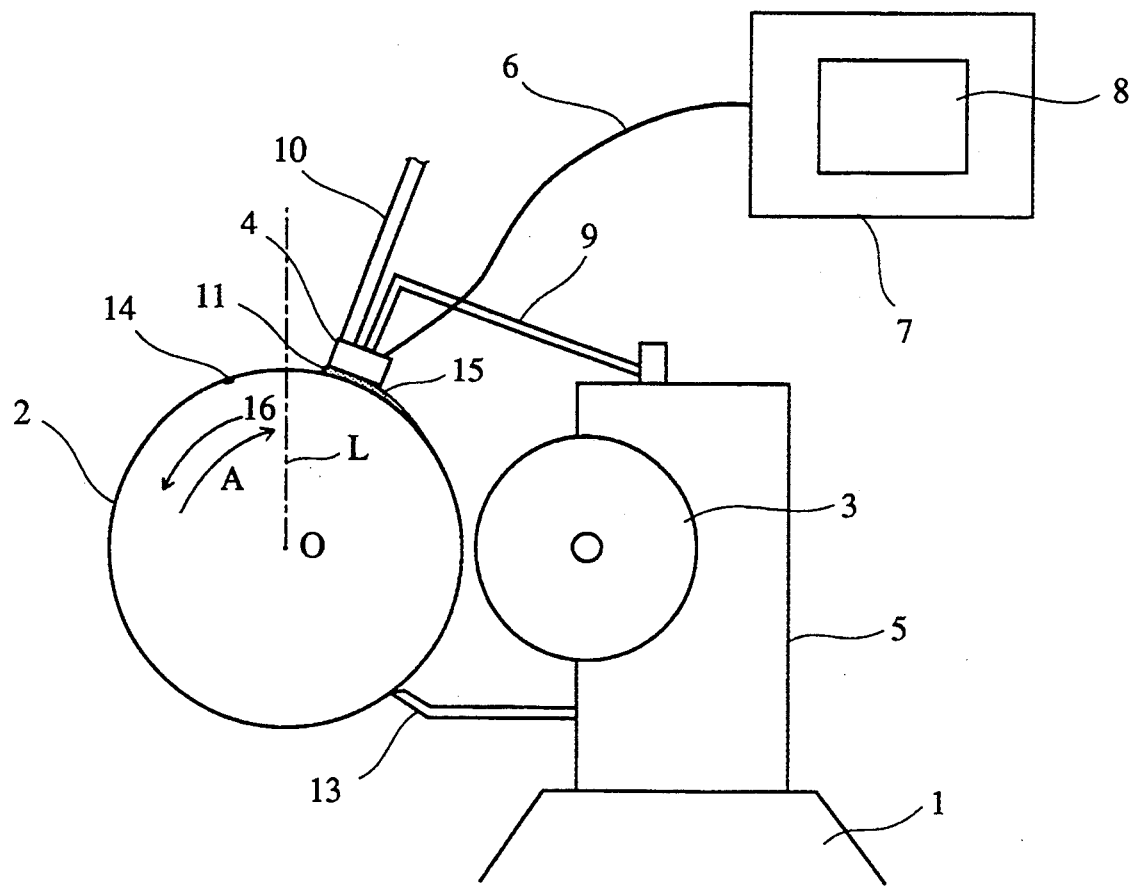
FIG. 1 is a schematic cross-sectional view showing an example of an apparatus for conducting the detection of defects in a surface portion of a cylindrical member with an ultrasonic wave according to the present invention.

FIG. 1 shows an example of the apparatus for detecting defects in a surface portion of a roll being ground by a grinder machine. In this apparatus, the roll 2 as a cylindrical metal member to be measured is rotatably supported, and a grinding wheel 3 for grinding the roll 2 is not in contact with the roll 2 while the detection of defects is conducted. A probe 4 is mounted via a supporting member 9 to a carriage 5 reciprocating on a work bed 1 such that it is in contact with a surface of the roll 2 via a thin film of a contact liquid medium 15. The rotational direction A of the roll 2 is opposite the propagation direction 16 of the surface ultrasonic wave. The probe 4 is positioned on the surface of the roll 2 on or slightly rearward with respect to the rotational direction A of the roll 2 than a vertical line L passing through a center O of the roll 2, in order to prevent the contact liquid medium 15 from falling from the surface of the roll 2 in the direction in which the ultrasonic wave propagates.

Figure 2:
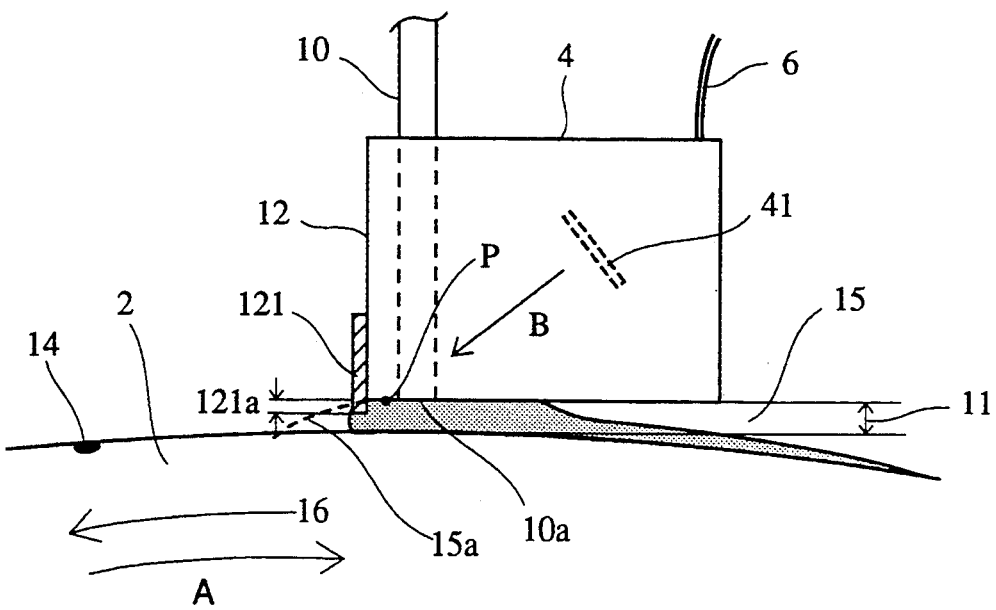
FIG. 2 is a view showing in detail the detection of defects in a surface portion of a rotating cylindrical member with the surface ultrasonic wave probe according to the present invention.

As shown in detail in FIG. 2, the probe 4 is provided with a pipe 10 having an opening 10a on a lower surface of the probe 4 for supplying a contact liquid medium 15 to a gap 11 between the surface of the roll 2 and the probe 4. The probe 4 is connected to an ultrasonic defect-detecting circuit 7 via a high-frequency cable 6. The ultrasonic defect-detecting circuit 7 is provided with a CRT 8 for monitoring and a printer (not shown). The size of the probe 4 is not particularly restricted, but it is preferable that a lower surface of the probe 4 is 20 mm to 70 mm in a rotational direction of the roll 2, and 10 mm to 50 mm in a transverse direction (axial direction of the roll 2).

A scraper 13 is mounted to the carriage 5 such that the scraper 13 is in contact with the surface of the roll 2 on a lower side of the roll 2 to remove the contact liquid medium 15 to keep the surface of the roll 2 clean.

FIG. 2 shows the details of the detection of defects in a surface portion of the rotating roll 2 with the probe 4 of the present invention. A center beam of the ultrasonic wave propagating in the direction B from an ultrasonic vibrator 41 in the probe 4 enters into the contact liquid medium 15 at an incident point P and then passes through the contact liquid medium 15 to the surface of the roll 2. The ultrasonic wave reached the roll 2 propagates in the direction 16 as a surface ultrasonic wave in the surface portion of the roll 2 to detect a defect 14.

When a lower surface of the probe 4, which can be brought into contact with cylindrical members having various diameters via the contact liquid medium 15, is stationary, a contact trace of the probe 4 on the cylindrical member extends linearly about the circumference of the cylindrical member to form a closed trace. When the detection of defects is made over the whole surface of the cylindrical member by moving the probe 4 on the reciprocating carriage, as described above, the contact trace of the probe 4 will extend linearly about the circumference of the cylindrical member to form a helical trace. In the present invention, it is important that there is a stable thin film of the contact liquid medium 15 in the gap 11 between the probe 4 and the roll 2, and that there should be as small an amount of the contact liquid medium 15 as possible between the incident point P and the surface of the roll 2 in the propagation direction of the ultrasonic wave to prevent the irregular reflection of the ultrasonic wave by the contact liquid medium 15.

From the above aspect, it is preferable that the opening 10a of the pipe 10 for supplying the contact liquid medium 15 is disposed near the incident point P on the rearward side thereof. In a preferred embodiment, the distance between the front end of the probe 4 and the pipe opening 10a is 1 mm to 20 mm, particularly, 3 mm to 10 mm. Incidentally, the contact liquid medium 15 is not restricted to a particular liquid, and it may be water, oil, a cutting liquid, etc.

The probe 4 is provided with a projection means 121 such as a small plate in a lower end portion of a front surface 12 of the probe 4 such that a lower end of the plate 121 slightly projects toward the thin film of the contact liquid medium 15. The plate 121 may be made of a metal such as stainless steel, carbon steel, or plastics. The plate 121 preferably has a thickness of 1–5 mm. It is preferable to mount the plate 121 to the probe 4 via screws, etc. so that the vertical position of the plate 121 can be adjusted freely. By the existence of the plate 121 slightly projecting from the lower surface of the probe 4, the thin film of the contact liquid medium 15 can be stably formed with an extremely reduced amount of the contact liquid medium 15 in the propagation direction of the ultrasonic wave.

In the above probe 4, the length of the projected portion 121a of the plate 121 may differ depending on the types of the contact liquid medium 15 used, but it is usually 30–50% of the gap 11. When the projected portion 121a of the plate 121 is as short as less than 30% of the gap 11, sufficient effect of preventing the expansion of the contact liquid medium 15 cannot be obtained. On the other hand, when the projected portion 121a is as long as more than 50% of the gap 11, the plate 121 is likely to accidentally come into contact with the roll 2. Incidentally, the gap 11 is depicted in FIG. 2 such that it has different thicknesses at the incident point P and at the middle point of the probe 4, but it should be noted that this apparent difference is due to the fact that the curve of the roll 2 is exaggerated. Therefore, there is no substantial difference in thickness between these two points.

The method of detecting defects in the surface portion of the cylindrical member by using the ultrasonic defect-detecting probe according to the present invention will be described below.

First, the probe 4 is positioned on the surface of the roll 2 with a gap 11 of 1.0 mm or less, preferably 0.3–0.5 mm. When the gap 11 exceeds 1.0 mm, the defect-detecting accuracy is low. Next, the contact liquid medium 15 is supplied to the pipe 10 having an opening 10a near the incident point P on the lower surface of the probe 4 to form the thin film of the contact liquid medium 15.

In this state, a beam of an ultrasonic wave is generated from the ultrasonic vibrator 41 in the probe 4 to enter into the thin film of the contact liquid medium 15 at the incident point P. A surface ultrasonic wave propagating through the surface portion of the roll 2 from the incident point P reaches a defect 14 by which the surface ultrasonic wave is reflected. The reflected surface ultrasonic wave is received by the ultrasonic vibrator 41 and a signal from the ultrasonic vibrator 41 is sent to the ultrasonic defect-detecting circuit 7 via a high-frequency cable 6. The signal of the reflected surface ultrasonic wave is visualized by the ultrasonic defect-detecting circuit 7 and displayed on the CRT 8 as a defect echo and printed out by a printer (not shown).

Since the probe 4 is movable by the carriage 5 along the rotational axis of the roll 2, defects can be detected along the entire length of the roll 2. Incidentally, in the process of detection of defects, the surface of the roll 2 is cleaned by the scraper 13.

If there is no small plate 121 projecting from the lower surface of the probe 4 toward the roll 2, the thin film of the contact liquid medium 15 is not stabilized, so that the thin film of the contact liquid medium 15 expands forward as shown by the dotted line 15a in FIG. 2. As a result, there is a large area of the contact liquid medium 15 on the forward side than the incident point P, which functions to reflect the surface ultrasonic wave irregularly. Thus, there is generated a large noise in the reflected surface ultrasonic wave, making it difficult to detect exactly the defects existing in the surface portion of the roll 2. However, by mounting the small plate 121 to the probe 4 such that it slightly projects downward in the contact liquid medium 15, the area of the contact liquid medium 15 existing on the forward side than the incident point P can be greatly reduced. As a result, noise of the reflected surface ultrasonic wave can be dramatically reduced.

The present invention will be explained in more detail referring to the following Examples without intention of restricting the scope of the present invention.

EXAMPLE 1

With the apparatus shown in FIG. 1 which contained the probe shown in FIG. 2, automatic defect-detecting test was conducted on a roll made of Ni—Cr alloyed cast iron having a body diameter of 770 mm, a body length of 1830 mm and an entire length of 3000 mm. The roll tested had defects A and B made artificially and a naturally-occurring defect C:

A: Slit (length in axial direction: 1 mm, and depth: 3 mm),

B: Vertical pore (diameter: 3 mm, and depth: 3 mm), and

C: Crack (length in axial direction: 2 mm, and depth: 1 mm).

The defect-detecting conditions are as follows:

Frequency: 2.25 MHz.

Sensitivity: Controlled such that a defect echo was as large as 80% at a position that the probe was separated by 150 mm from an artificial defect having a diameter of 2 mm and a depth of 2 mm in an STB-A2 test piece, and then the sensitivity was raised to 18 dB.

Detection pitch: 20 mm/rotation.

Roll rotation: 25 rpm.

As a result of the above tests, all of the defects A–C could be detected with the same accuracy as that of the manual method for detecting defects with a surface ultrasonic wave. The detection time was only about 4 minutes in the case of the method of the present invention while it was about 30 minutes in the case of the manual method for detecting defects with a surface ultrasonic wave. Thus, it can be concluded that the detection of defects with the surface ultrasonic wave probe of the present invention is as fast as about 8 times the manual method for detecting defects with a surface ultrasonic wave.

As explained in detail above, since the surface ultrasonic wave probe of the present invention is provided with a projection means slightly extending downward from a lower surface of the probe, the thin film of the contact liquid medium is stably formed, and there is substantially no thin film of the contact liquid medium on a surface of a portion of the cylindrical member in which the surface ultrasonic wave propagates. As a result, by bringing the probe into contact with the rotating cylindrical member via the contact liquid medium at an incident point of an ultrasonic wave, and by causing the surface ultrasonic wave to propagate in a direction opposite the rotational direction of the cylindrical member, high detection precision can be achieved at a high speed (for instance, about 8 times as fast as the conventional manual method for detecting defects with a surface ultrasonic wave). Also, there is no failure to detect any defects in the surface portion of the cylindrical member without operational difficulty.

What is claimed is:

1. A surface ultrasonic wave probe for use in the detection of defects in a surface portion of a cylindrical member by a method in which said probe is brought into contact with a surface of a rotating cylindrical member via a thin film of a contact liquid medium disposed in a gap between said probe and said cylindrical member such that a contact trace of said probe extends linearly about the circumference of said cylindrical member, and an ultrasonic wave propagates in the surface portion of said cylindrical member from said probe in an opposite direction to the rotational direction of said cylindrical member, said probe being provided in a front portion thereof with a projection means slightly extending downward from a lower surface of said probe so that said thin film of said contact liquid medium is stably formed, and that there is substantially no thin film of said contact liquid medium on a surface of a portion of said cylindrical member in which said surface ultrasonic wave propagates.

2. The surface ultrasonic wave probe according to claim 1, wherein said projection means extends downward by 30–50% of said gap.

3. A surface ultrasonic wave apparatus comprising (a) a member for rotatably supporting a cylindrical member to be tested; (b) a carriage capable of reciprocating along the axis of said cylindrical member; (c) a surface ultrasonic wave probe supported by said carriage such that the probe is brought into contact with a rotating cylindrical member via a contact liquid medium disposed in a gap between said probe and said cylindrical member, said probe generating an ultrasonic wave propagating in the surface portion of said cylindrical member as a surface ultrasonic wave in an opposite direction to the rotational direction of said cylindrical member; and (d) a pipe mounted to said probe and having an opening located on a lower surface of said probe near a front end thereof for supplying said contact liquid medium into a gap between said probe and said cylindrical member, said probe being provided in a front portion thereof with a projection means extending downward from a lower surface of said probe so that a thin film of said contact liquid medium is stable formed, and that there is substantially no thin film of said contact liquid medium on a surface of a portion of said cylindrical member in which said surface ultrasonic wave propagates.

4. The surface ultrasonic wave apparatus according to claim 3, wherein said projection means extends downward by 30–50% of said gap.

* * * * *